United States Patent
Venkateswarlu et al.

(10) Patent No.: US 7,626,025 B2
(45) Date of Patent: Dec. 1, 2009

(54) BETA-CARBOLINE DERIVED GUANIDINE ALKALOIDS, TIRUCHENDURAMINE

(75) Inventors: Yenamandra Venkateswarlu, Hyderabad (IN); Kodela Ravinder, Hyderabad (IN); Jhillu S. Yadav, Hyderabad (IN); Yandrapu Sarathkumar, Hyderabad (IN); Sistla Ramakrishna, Hyderabad (IN); Prakash V. Diwan, Hyderabad (IN); Janapala V. Rao, Hyderabad (IN); Ratnam Ramesh, Hyderabad (IN); Hartmut Laatsch, Gottingen (DE)

(73) Assignees: Council of Scientific and Industrial Research, New Delhi (IN); Department of Ocean Development, New Delhi (IN)

( * ) Notice: Subject to any disclaimer, the term of this patent is extended or adjusted under 35 U.S.C. 154(b) by 136 days.

(21) Appl. No.: 10/814,777

(22) Filed: Mar. 30, 2004

(65) Prior Publication Data

US 2005/0222168 A1 Oct. 6, 2005

(51) Int. Cl.
C07D 455/04 (2006.01)
A61K 31/437 (2006.01)
(52) U.S. Cl. .......................... 546/80; 514/292
(58) Field of Classification Search ............... 514/292; 546/80
See application file for complete search history.

(56) References Cited

FOREIGN PATENT DOCUMENTS

WO  WO 03/033496 A1  4/2003
WO  WO 03/065036 A1  8/2003

OTHER PUBLICATIONS

Davidson, Bradley S., "Ascidians: Producers of Amino Acid Derived Metabolites", Chem. Rev., 1993, vol. 93, No. 5, pp. 1771-1791.
Ortega, Maria J., et al., "New Rubrolides from the Ascidian Synoicum blochmanni", Tetrahedron, vol. 56, No. 24, Jun. 2000, pp. 3963-3967.
Reddy, M. Venkata Rami, et al., "New Lamellarin Alkaloids from an Unidentified Ascidian from the Arabian Sea", Tetrahedron, vol. 53, No. 10, Mar. 10, 1997, pp. 3457-3466.

*Primary Examiner*—Rita J Desai
(74) *Attorney, Agent, or Firm*—Darby & Darby

(57) ABSTRACT

A novel β-carboline guanidine derivative tiruchenduramine (1)

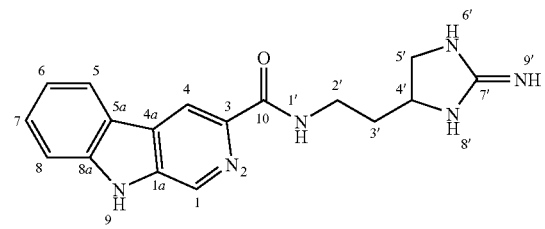

and its derivatives are disclosed. These compounds have been isolated from the Indian ascidian *Synoicum macroglossum*. These compounds are useful in the treatment of diabetic disorder by providing inhibition of α (alpha)glucosidase.

27 Claims, No Drawings

BETA-CARBOLINE DERIVED GUANIDINE ALKALOIDS, TIRUCHENDURAMINE

FIELD OF THE INVENTION

The present invention relates to a novel chemical compound and more particularly, the β-carboline derived guanidine alkaloid, tiruchenduramine (1) and derivatives (2-20), derived from an ascidian. These compounds are useful as α-Glucosidase Inhibitors.

BACKGROUND OF THE INVENTION

The most challenging goal in the management of patients with diabetes mellitus is to achieve blood glucose levels as close to normal as possible. Postprandial hyperglycemia (PPHG) is an independent risk factor for the development of macro vascular complications of diabetes mellitus. Alpha (α) glucosidases are a group of enzymes that catalyze the final step in the digestive process of carbohydrates, and hence alpha glucosidase inhibitors could retard the use of dietary carbohydrates to suppress PPHG. Alpha glucosidase inhibitors target the alpha glucosidases such as sucrase, maltase, glycoamylase dextranse and isomaltases and to reduce Postprondial hyperglycemia primarily by interfering with the carbohydrate digesting enzymes and delaying glucose absorption.

SUMMARY OF THE INVENTION

The present invention relates to a novel chemical compound and more particularly, the β-carboline derived guanidine alkaloid, tiruchenduramine (1) and derivatives (2-20), derived from an ascidian. These compounds are useful as α-Glucosidase Inhibitors.

Marine ascidians have been the focus of intensive chemical investigation in recent years and they are very rich sources for unique and biologically active secondary metabolites. [(Davidson, B. S., Chem. Rev. 1993, 93, 1771-1791.) & (Faulkner, D. J. Nat. Prod, Rep. 1993, 10, 197; 1994, 11, 355; 1995, 12, 223; 1996, 13, 75; 1997, 14, 4; 1998, 15, 13. 1999, 16, 155. 2000, 17, 7. 2001, 18, 1. 2002, 19, 1.)] A major group of those metabolites are nitrogen containing compounds, particularly aromatic heterocyclic compounds. As part of our ongoing investigation on bioactive compounds from marine organisms [(Reddy, M. V. R.; Faulkner, D. J.; Venkateswarlu, Y. and Rao, M. R.; Tetrahedron. 1997, 53, 3457). & (Reddy, M. V. R.; Rao, M, R.; Rhodes, D.; Hansen, M.; Rubbins, K.; Bhushman, F.; Venkateswarlu, Y. and Faulkner, D. J. J. Med. Chem. 1999, 42, 1901.)] we describe the isolation of a novel β-carboline guanidine derivative tiruchenduramine of the Formula (1)

from the ascidian *Synoicum macroglassum*. *Synoicum macroglossum* was collected at Tiruchendur, Tamilnadu, India during February 2002. A literature survey revealed that the genus *Synoicum macroglossum* has yielded several tetraphenolic bis-spiroketals and different rubrolide compounds. [(Carroll, A. R.; Healy, P. C.; Quinn, R. J. and Tranter, C.; *J. Org. Chem.* 1999, 64, 2680.) & (Ortega, M. J.; Zubia, E.; Ocana, J. M.; Naranjo, S and Salva, *J. Tetrahedron.* 2000, 56, 3963.)].

In the present invention, freeze-dried ascidian *Synoicum macroglossum* was subjected to solvent extraction using DCM: Methanol (1:1). The extract so obtained was partitioned between water and EtOAc. The water extract was lyophilized and the residue was triturated with MeOH. The MeOH soluble material was subjected to gel filtration (Sephadex, LH-20), followed by silica gel column chromatography eluting with $CHCl_3$: MeOH (80:20%) to yield tiruchenduramine of the Formula (1). The compounds of the present invention have excellent application are useful as α-Glucosidase Inhibitors.

DETAILED DESCRIPTION

Structure Elucidation of Tiruchenduramine (1)

In the mass spectrum, the compound of Formula 1 showed a molecular mass of 322, corresponding to $C_{17}H_{18}ON_6$. The UV spectrum in methanol showing absorptions at $\lambda_{max}$ 215, 234, 270, 334, and 347 nm corresponded to the β-carboline chromophore, [Gozler, T., Gozler, B.; Linden, A.; Hesse, M. *Phytochemistry.* 1996, 43,1425.]

The structure of compound 1 was established by the study of $^1H$—$^1H$—COSY, HMQC, HMBC and NOESY spectral data (Table 1) as Formula 1. Tiruchenduramine of the formula 1 was tested for anti-diabetic activity by an in-vitro assay and was found that it inhibits α-glucosidase at 78.8 μg.

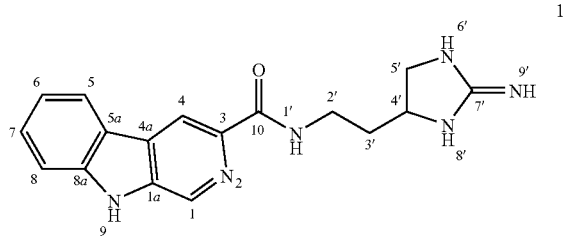

FIG. 1

TABLE 1

| | Spectral data of Compound 1 | | | |
|---|---|---|---|---|
| S. NO. | $^{13}C$ NMR$^a$ | $^1H$ NMR$^b$ | $^1H$-$^1H$ COSY | HMBC |
| 1 | 132.22 | 8.85 (1H, s) | — | C-3, C-4a, C-1a |
| 2 | — | — | — | — |
| 3 | 139.52 | — | — | — |
| 4 | 113.88 | 8.81 (1H, s) | — | C-3, C-10, C-5a, C-4a, C-1a |
| 4a | 128.06 | — | — | — |
| 5a | 120.87 | — | — | — |
| 5 | 122.08 | 8.20 (1H, d) | H-6 | C-5a, C-8a, C-7 |
| 6 | 119.88 | 7.28 (1H, t) | H-5, H-7 | C-7, C-8a, C-8 |
| 7 | 128.53 | 7.58 (1H, t) | H-6, H-8 | C-5, C-8a |
| 8 | 112.24 | 7.63 (1H, d) | H-7 | C-5a, C-6 |
| 9 | — | 12.10 (1H, br s) | — | — |

TABLE 1-continued

Spectral data of Compound 1

| S. NO. | $^{13}$C NMR$^a$ | $^{1}$H NMR$^b$ | $^{1}$H-$^{1}$H COSY | HMBC |
|---|---|---|---|---|
| 10 | 165.14 | — | — | — |
| 1' | — | 8.84 (1H, s) | — | C-10 |
| 2' | 35.23 | 3.42 (2H, m) | H-3' | C-10, C-3', C-4' |
| 3' | 34.93 | 1.82 (2H, m) | H-2', H-4' | C-2', C-4', C-5' |
| 4' | 52.95 | 3.99 (1H, m) | H-3', H-5' | C-3', C-2', C-5', C-7' |
| 5' | 47.93 | 3.77 (1H, dd), 3.25 (1H, dd) | H-4' | C-4', C-3', C-7' |
| 6', 8', 9' | — | 7.80 (2H, br s), 8.18 (1H, br s) | — | — |
| 7' | 159.19 | — | — | — |

$^a$75 MHz and
$^b$300 MHz, DMSO-d$_6$

Tiruchenduramine (1) and its various derivatives are shown below:

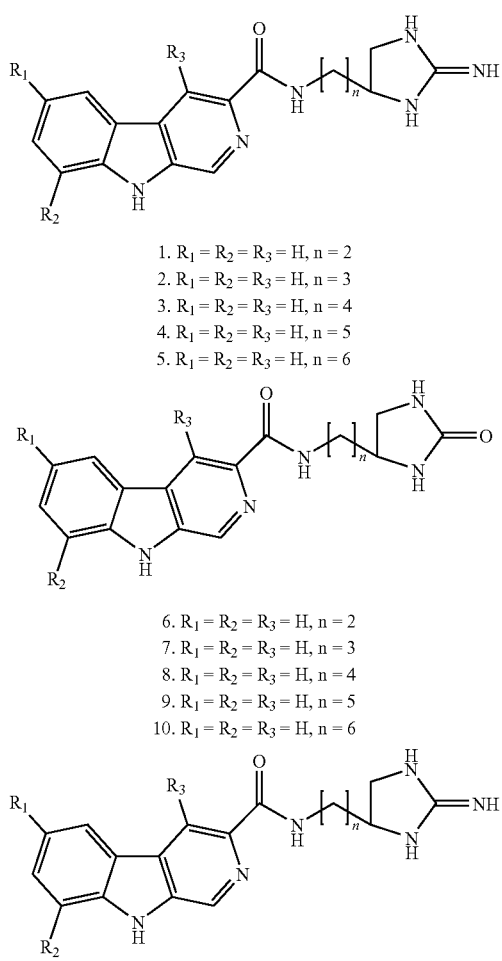

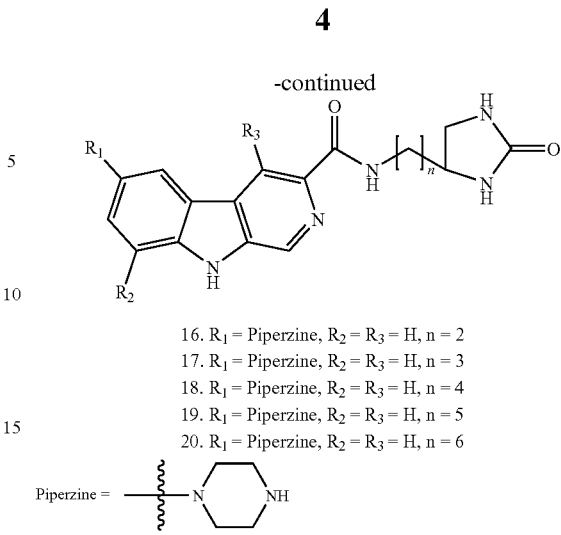

FIG. 2

It has been discovered that tiruchenduramine (1) and various derivatives of tiruchenduramine (2-20) shown in FIG. 2 above can function as effective anti-diabetic agents.

In a first aspect, the invention features an alkaloid according to the structure of formula 1 and tautomers, anhydrides, and salts thereof. In another embodiment, the compound according to formula 1 can be of different structural analogues such that structures 2 to 20 and their derivatives ma have substitutions at C-1 or C-4, or C-5 or C-8 with substituents halogens (Br, I, F) or amine, amino, imino, carboxylic acid or amides. The alkaloid molecule may be designed to be capable of traversing biological membrane. In one aspect, the invention features a pharmaceutical composition in unit dosage form suitable for management of diabetic disorder. The composition consists essentially of about 78.8 μg of the compound 1 and derivatives (2-20) thereof. The unit dosage of the composition may be, for example, from about 15 mg to about 315 mg or from about 24 mg to about 280 mg. The composition is useful for the treatment of a wide variety of diabetic disorders particularly in postprondial hyperglycemic states. The invention also features an article of manufacture including packaging material and a pharmaceutical agent contained therein that is therapeutically effective for the management of diabetic disorder in a mammal. The packaging material may include a label that indicates that the pharmaceutical agent can be used for suppressing the diabetic disorder in a mammal. The pharmaceutical agent includes tiruchenduramine or a derivative thereof.

In another embodiment, the present invention provides a method of obtaining the compounds 1-20 and derivatives thereof. The method includes extracting the compound from ascidian, such for example, *Synoicum macroglossum*. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patent, and other references mentioned herein are incorporated by reference in their entirety. In case of conflict, the present specification, including definitions, will control. In addition, the materials, methods, and examples are illustrative only and not intended to be limiting. Other features and advantages of the invention will be apparent from the following detailed description, and from the claims.

The invention provides a novel β-carboline derived guanidine alkaloid of the formula 1. Thus, in a first embodiment, the present invention provides a novel compound with structure 1 or derivatives (2-20) shown in FIG. 2 above, stereoisomer or pharmaceutically acceptable salts thereof. In another embodiment, the structure 1 shown in FIG. 2 above, is modified at various places of the structure resulting in compounds (2-20) as shown in FIG. 2 above. However, modifications to structure 1 in FIG. 2 will be apparent to those of skill in the art and are within the skill of those in the art. Additionally, modification of the stereochemistry of the above formulas is also within the skill of those in the art. For example, at C1 to C10 and from N 1' to N-9' and stereochemistry at C-4' can be either R— or S—. such stereo-chemical substitutions are applicable at C-4' present compounds (1-20) so long as the compound retains its biological activity. By "biological activity" is meant the ability of the compound to inhibit, suppress or modulate diabetes or other diseases or disorders such as postprondial hyperglycemia.

The structures of 1-20 illustrated in FIG. 2 above are capable of forming pharmaceutically acceptable salts, including acid addition salts and base salts, as well as solvates, such as hydrates and alcoholates. All of these pharmaceutical forms are contemplated by this invention and are included herein. Acid addition salts are readily formed as compounds 1-20 shown in FIG. 2 above contain amino substituent groups, or when nitrogen atoms are present. Base salts can be formed when carboxylic acid substituent groups are present. Pharmaceutically acceptable acid addition salts of the compounds 1-20 shown in FIG. 2 above include salts derived from inorganic acids such as hydrochloric, nitric, phosphoric, sulfuric, hydrobromic, hydriodic, phosphoric, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, bezenesulfonate, toluenesulfonate, phenylacetate, citrate, lactate, maleate, tartrate, methanesulfonate, and the like. Also contemplated are salts of amino acids such as arginate and the like, gluconate, and galacturonate (see, for example, Berge S. M., et al., "Pharmaceutical Salts," J. of Pharmaceutical Science, 1977; 66:1-19). The acid addition salts of basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention. Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge S. M., et al., "Pharmaceutical Salts," J. of Pharmaceutical Science, 1977; 66:1-19).

The base addition salts of acidic compounds are prepared by contacting the free acid form with a sufficient amount of the desired base to produce the salt in the conventional mar. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organicacids. The pharmaceutically acceptable salts of the present invention can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are used. Lists of suitable salts are found in Remington's Pharmaceutical Sciences, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Prodrugs" are also encompassed by the present specification and are intended to include any covalently bonded carriers which release the active parent drug according to formula 1 to 20 in viva when such prodrug is administered to a mammalian subject. The mammal is preferably a human. Prodrugs of a compound of formula 1 to 20 in FIG. 2 above are prepared by modifying functional groups present in the compound in such a way that the modifications are cleaved, either in routine manipulation or in vivo, to the parent compound. Prodrugs include compounds of formula 1 to 20 wherein a hydroxy, amino, or sulfhydryl group is bonded to any group that, when the prodrug or compound of formula 1 to 20 in FIG. 2 above is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula 1 to 20 and the like.

The invention provides compounds that suppress postprondial glucose levels in the management of diabetic disorders in a human subject. In addition, various alkaloids may be made from tiruchenduramine using a range of chemistries. For example, mono/di halo (Bromo or fluoro or iodo) or amino/ nitro or tiruchenduramine derivatives may be produced by selective reactions, Additionally derivations will be recognized and are routine to those of skill in the art. The invention also relates to a method of suppressing diabetic responses in a subject comprising administering a compounds 1 to 20 mentioned in FIG. 2 above to subject in need thereof. In particular, the compound is tiruchenduramine or a derivative thereof. The subject is a mammal or a human. The compounds can be administered orally, intravenously, intraperitoneally, intrapleurally, intrathecally, subcutaneously, intramuscularly, intranasally, through inhalation or by suppository, depending on the situation of the patient and on various indications. Tiruchenduramine or a derivative thereof may be administered in a daily amount of from about 15 mg to about 480 mg. Typically the dosage ranges from about 0,5 mg/kg to about 7 mg/kg. In extreme conditions, up to about 20 mg/kg of tiruchenduramine or a derivative thereof may be administered. Once administered, these compounds act as anti-diabetic agents. Without being bound by any particular theory or biochemical mechanism, these compounds inhibit alpha glucosidase, which is responsible for catalyzing the final step in the digestive process of carbohydrates and thus preventing reabsorption of glucose. Thus the compounds inhibit glucose absorption and prevent the postprondial hyperglycemia in diabetic conditions.

The actual dosage of tiruchenduramine or derivatives thereof, formulation or composition that modulates diabetic disorder depends on many factors, including the size and health of an individual. However, one of ordinary skill in the art can use the following teachings describing the methods and techniques for determining clinical dosages (Basics of Clinical Pharmacology, Ed: Bertarm G Katzung, $8^{th}$ edition, Lange books/ McGraw Hill, Medical Publishing Division, New York, pages 711-734; Clinical Pharmacology, Laurence D R, Bennett P N and Brown M J, $8^{th}$ Edition, Churchill Livingstone, New York, pages 615-632; Pharmacology, Rang H P, Dale M M and Ritter J M, $4^{th}$ edition, Churchill Livingstone, New York, pages 385-398 and Pharmacological Basis of Therapeutics, Goodman and Gilman, McGraw Hill Health Professional Division, New York, Pages 1487-1517).

In an alternative embodiment, a pharmaceutical composition containing from about 15 mg to about 480 mg of tiruchenduramine or a derivative thereof is provided in unit dosage form. The dose may be divided into 1-3 daily doses. Typical dosages of these pharmaceutical composition range from about 0.5 mg/kg to about 7 mg/kg. In extreme conditions, up to about 20 mg/kg may be administered. Lyophilized tiruchenduramine and lyophilized pharmaceutically acceptable salts are particularly useful as pharmaceutical compositions. The optimal concentration of tiruchenduramine or a derivative thereof in a pharmaceutically acceptable composition may vary, depending on a number of factors, including the preferred dosage of the compound to be administered, the chemical characteristics of the compounds employed, the formulation of the compound excipients and the route of administration. The optimal dosage of a pharmaceutical composition to be administered may also depend on such variables as the type and extent of the diabetic disorder, the overall health status of the particular subject and the relative biological efficacy of the compound selected. These compositions may be used for the treatment of diabetic conditions including, but not limited to postprondial hyperglycemia and macro vascular complications of diabetes mellitus. An "effective amount" or "alpha glucosidase inhibiting amount" means that amount of the compound necessary to modulate, inhibit, or suppress postprondial hyperglycemia in the diabetic conditions.

Compounds of the invention may be formulated into pharmaceutical compositions by admixture with pharmaceutically acceptable non-toxic excipients or carriers. Such compounds and compositions may be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Sustained release compositions are also encompassed by the present invention. Compositions for other routes of administration may be prepared as desired using standard methods.

A compound of the invention may be conveniently administered in unit dosage form, and may be prepared by any of the methods well known in the pharmaceutical art for example, as described in Remington's Pharmaceutical Sciences (Mack Pub. Co., Easton, Pa., 1990). Formulations for parenteral administration may contain as common excipients sterile water or saline, polyalkylene glycols such as polyethylene glycol, oils of vegetable origin, hydrogenated naphtalenes, and the like. In particular, biocompatible, biodegradable lactide polymer, lactide/glycolide copolymer, or polyoxethylene-polyoxypropylene copolymers are examples of excipients for controlling the release of a compound of the invention in vivo. Other suitable parenteral delivery systems include ethylene-vinyl acetate copolymer particles, osmotic pumps, implantable infusion systems, and liposomes. Formulations for inhalation administration may contain excipients such as lactose, if desired. Inhalation formulations may be aqueous solutions containing, for example, polyoxyethylene-9-lauryl other, glycocholate and deoxycholate, or they may be oily solutions for administration in the form of nasal drops, If desired, the compounds can be formulated as a gel to be applied intranasal. Formulations for parenteral administration may also include glycocholate for buccal administration.

The invention also relates to an article of manufacturing containing packaging material and tiruchenduramine or a derivative thereof contained within the packaging material. Tiruchenduramine or derivatives thereof are therapeutically effective for suppressing postprondial hyperglycemia in a subject. The packaging material may contain a label or package insert indicating that tiruchenduramine or a derivative thereof may be used for suppressing postprondial hyperglycemia in a subject.

In an alternate embodiment, the invention relates to compositions and kits comprising a first chemotherapeutic agent including tiruchenduramine or a derivative thereof and a second therapeutic agent. The second therapeutic agent is not tiruchenduramine or a derivative thereof. These compositions are effective to suppress postprondial hyperglycemia in a subject. Various classes of therapeutic agents, including alkylating agents, antimetabolites, vinca alkaloids, antibiotics, cytokines, growth factors, non-steroidal anti-inflammatory drugs, such as aspirin, may be used in the composition.

Yet in another embodiment, tiruchenduramine is administered in type I or type II diabetic conditions for synergistic action thereby reducing the regular dose of insulin or oral antidiabetic agents in the management of diabetes mellitus.

Also provided are methods for obtaining the compounds of formulae 1 to 20. Such methods include chemical synthesis as well as extraction techniques. For example, tiruchenduramine (1) can be extracted from an ascidian (e.g. such as the *Synoicum macroglossum*). Such extraction techniques include for example, methanol extraction followed by a dichloromethane: methanol extraction and purification on a Sephadex LH-20 column, by standard chromatography techniques. Other methods of extracting the compound from an ascidian will be apparent to those of skill in the art. For example, modifications in column packing, elution buffers flow rates for eluting the compound may all be modified or changed, Such modifications are routine to those of skill in the art.

The invention will be further described in the following examples, which do not limit the scope of the invention described in the claims:

Extraction and Isolation

The freshly collected ascidian specimens were soaked in MeOH at the site of collection and kept in MeOH until workup. The sponge *Synoicum macroglossum* (1.5 kg) was extracted with 1:1 $CH_2Cl_2$—MeOH (3×3L) at room temperature. The combined extracts including the initial methanol extract were filtered, and the solvent was removed under reduced pressure to give a predominantly aqueous suspension, which was partitioned between water and EtOAc. The water extract was lyophilized and triturated with MeOH, this extracted methanol portion concentrated under reduced pressure to give a dark brown gummy mass (3 gm). This crude extract was subjected to gel filteration chromatography (Sephadex LH-20, 1:1 $CH_2Cl_2$—MeOH, collecting different fractions, in this, selected fractions were subjected to silica gel chromatography using a gradient of $CHCl_3$—MeOH, to yield β-carboline Guanidine compound of the Formula 1. The EtOAc soluble portion was again concentrated under reduced pressure to give a dark brown gummy mass (2 g). This crude extract was subjected to gel filtration chromatography (Sephadex LH-20), by using with 1:1 $CH_2Cl_2$—MeOH, solvent system, collecting different fractions (25 mL each) followed by silica gel chromatography of selected fractions using a step gradient of hexane to hexane-ethyl acetate mixtures to MeOH, to yield tiruchenduramine of formula 1. Compound of formula 1 was obtained as optically active solid (30 mg), IR (KBr) $v_{max}$: 3221, 1681 and 1622. UV (MeOH), $\lambda_{max}$ 215, 234, 270, 334, and 347 nm. $^1$H-NMR (300 MHz DMSO-d6), $^{13}$C-NMR (75 MHz, DMSO-d6) see table-1, positive FABMS m/z 323

The invention claimed is:
1. A purified compound having the following formula

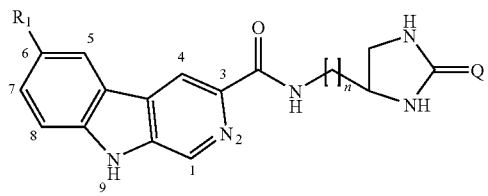

wherein the compound is isolated from an ascidian;
n is 2 to 6; Q is NH or O;
$R_1$ is H or piperazine;
and tautomers, stereoisomers, anhydrides, and pharmaceutically acceptable salts thereof.

2. A process for the preparation of a compound according to claim 1, which comprises subjecting an ascidian to solvent extraction.

3. A process as in claim 2 wherein said ascidian is *Synoicum macroglossum*.

4. A process as claimed in claim 2, wherein said extraction comprises extraction in the presence of methanol followed by a dichloromethane:methanol extraction and the extract so obtained is subject to purification.

5. A process as claimed in claim 4, wherein said ascidian comprises freeze dried *Synoicum macroglossum*.

6. A process as claimed in claim 5, wherein said dichloromethane and methanol are used in a ratio of 1:1.

7. A process as claimed in claim 6, wherein after extraction with dichloromethane and methanol, the extract so obtained is partitioned between water and ethyl acetate.

8. A process as claimed in claim 7, wherein said water extract is lyophilized and the residue is triturated with methanol.

9. A process as claimed in claim 4 wherein said purification comprises a Sephadex LH-20 column chromatography.

10. A pharmaceutical composition comprising as an active ingredient a compound according to claim 1, and a pharmaceutically acceptable carrier, vehicle or excipient.

11. A composition as claimed in claim 10, wherein said active ingredient is present in an amount of about 78.8 µg.

12. A composition as claimed in claim 10, wherein the unit dosage of said composition is from about 15 mg to about 480 mg.

13. A composition as claimed in claim 12, wherein the unit dosage of said composition is from about 24 mg to about 280 mg.

14. A process as claimed in claim 3, wherein said extraction comprises extraction in the presence of methanol followed by a dichloromethane:methanol extraction and the extract so obtained is subject to purification.

15. A process as claimed in claim 14, wherein said ascidian comprises freeze dried *Synoicum macroglossum*.

16. A process as claimed in claim 15, wherein said dichloromethane and methanol are used in a ratio of 1:1.

17. A process as claimed in claim 16, wherein said extraction with dichloromethane and methanol, the extract so obtained is partitioned between water and ethyl acetate.

18. A process as claimed in claim 17, wherein said water extract is lyophilized and the residue is triturated with methanol.

19. A process as claimed in claim 5, wherein said purification comprises a Sephadex LH-20 column chromatography.

20. A process as claimed in claim 6, wherein said purification comprises a Sephadex LH-20 column chromatography.

21. A process as claimed in claim 7, wherein said purification comprises a Sephadex LH-20 column chromatography.

22. A process as claimed in claim 8, wherein said purification comprises a Sephadex LH-20 column chromatography.

23. A process as claimed in claim 14, wherein said purification comprises a Sephadex LH-20 column chromatography.

24. A process as claimed in claim 15, wherein said purification comprises a Sephadex LH-20 column chromatography.

25. A process as claimed in claim 16, wherein said purification comprises a Sephadex LH-20 column chromatography.

26. A process as claimed in claim 17, wherein said purification comprises a Sephadex LH-20 column chromatography.

27. A process as claimed in claim 18, wherein said purification comprises a Sephadex LH-20 column chromatography.

* * * * *